United States Patent [19]

Young, Jr.

[11] Patent Number: 4,814,481

[45] Date of Patent: Mar. 21, 1989

[54] ISOMERIZATION OF FUMARONITRILE AND MALEONITRILE

[75] Inventor: Harold W. Young, Jr., Midland, Mich.

[73] Assignee: The Dow Chemical Company, Midland, Mich.

[21] Appl. No.: 125,913

[22] Filed: Nov. 27, 1987

[51] Int. Cl.$^4$ .................. C07C 120/00; C07C 121/20
[52] U.S. Cl. ..................................................... 558/356
[58] Field of Search ......................................... 558/356

[56] References Cited

U.S. PATENT DOCUMENTS

| | | | |
|---|---|---|---|
| 2,447,810 | 8/1948 | Mowry | 260/78.5 |
| 2,478,285 | 8/1949 | Langkammerer | 558/356 |
| 2,695,912 | 11/1954 | Hartig | 558/356 |
| 2,751,407 | 6/1956 | Foster et al. | 558/356 |
| 3,313,840 | 4/1967 | Kosel et al. | 558/383 |
| 3,959,345 | 5/1976 | Morita et al. | 558/334 |
| 4,436,671 | 3/1984 | Furuoya et al. | 558/325 X |

FOREIGN PATENT DOCUMENTS 2041221  8/1970  Fed. Rep. of Germany .

OTHER PUBLICATIONS

*Tetrahedron Letters* No. 44, pp. 3909-3912 (1969); Jones et al.
*Journal of the Chemical Society* 1958, 3879-3886 (1958); Ficken et al.
*Journal of the American Chemical Society* 92, 1318-1326 (1970) Dalton et al.
*Chemical Physics Letters* 121, 386-389 (1985); Kruppa et al.
*Makromol. Chem.* 179, 101-108 (1978); Helling et al.
*The Journal of Organic Chemistry* 34, 3562-3565 (1969); Turro et al.
*Bulletin of the Korean Chemical Society* 6, 176-177 (1985); Kim et al.
*Journal of the Chemical Society* 1958, 4839-4846 (1958); Linstead et al.
*Bull Soc Chim Belg* 46, 199-210 (1936); Jennen.

Primary Examiner—Joseph Paul Brust
Attorney, Agent, or Firm—Paula Sanders Ruhr

[57] ABSTRACT

Fumaronitrile or maleonitrile in a nitrile solvent in the presence of a base isomerizes to its geometric isomer. This process is particularly useful for the preparation of maleonitrile by the isomerization of fumaronitrile in acetonitrile in the presence of solid potassium hydroxide. The unreacted fumaronitrile and acetonitrile may be recycled.

20 Claims, No Drawings

ISOMERIZATION OF FUMARONITRILE AND MALEONITRILE

BACKGROUND OF THE INVENTION

This invention relates to isomerization reactions of fumaronitrile and maleonitrile and particularly to processes for the preparation of maleonitrile.

Maleonitrile and fumaronitrile are useful as intermediates in the production of pharmaceuticals, industrial chemicals and various other useful compounds and as a starting monomer for polymer synthesis. For example, maleonitrile is useful as an intermediate in the preparation of such compounds as pyridoxine and its related compounds, 3- or 5-aminoisoxazoles, nitrogen-containing compounds such as purine and pyrimidine bases.

Various methods exist for the production of maleonitrile and fumaronitrile. U.S. Pat. No. 4,436,671 discloses an improved method of producing unsaturated aliphatic dinitriles such as fumaronitrile and maleonitrile by the ammoxidation of $C_4$ straight chain hydrocarbons in the presence of a catalyst where the improvement is using a catalyst comprising at least one oxide of vanadium and tungsten, at least one oxide of antimony, phosphorus and boron, and at least one oxide of chromium, nickel, aluminum or silicon. U.S. Pat. No. 3,313,840 discloses a process for the preparation of a mixture of fumaronitrile and maleonitrile by the catalytic dehydrogenation of succinonitrile in the presence of oxygen. Linstead et al., *J. Chem. Soc.*, p. 4839 (1958), disclose a process for the preparation of maleonitrile by the dehydration of amides using phosphorus oxychloride in ethylene dichloride. U.S. Pat. No. 3,959,345 teaches that maleonitrile may be produced by the reaction of hydrogen cyanide with cyanoacetylene.

In addition, approaches for the preparation of maleonitrile include the isomerization of fumaronitrile to yield maleonitrile. For example, U.S. Pat. No. 2,447,810 teaches that fumaronitrile isomerizes to produce maleonitrile when heated with an iodine catalyst. Kruppa et al., *Chem. Phys. Lett.*, 121, 386–389 (1985), and Dalton et al., *J. Am. Chem. Soc.*, 92, 1318–1326 (1970), discuss the photo-initiated isomerization of fumaronitrile to maleonitrile. The isomerization of fumaronitrile to maleonitrile in the presence of butyl lithium in tetrahydrofuran is discussed by Helling et al., *Makromol. Chem.* 179, 101–108 (1978). It has also been reported that the maleonitrile is isomerized to fumaronitrile by aqueous hydrogen chloride and that it isomerizes spontaneously over a long period of time. Linstead et al., *J. Chem. Soc.*, 4839 (1958).

All of these methods concerning the production or isomerization of maleonitrile and fumaronitrile have some problems. These problems include the formation of various by-products, the difficulty of working on an industrial scale, the necessity of removing and recovering expensive catalysts and little control over whether maleonitrile or fumaronitrile is produced or in what proportions maleonitrile and fumaronitrile are produced. Therefore, what is needed is a simple process for the preparation of maleonitrile or fumaronitrile that uses simple and relatively inexpensive reactants, that produces few by-products, and that can convert fumaronitrile to maleonitrile or vice versa or shift the percentage of maleonitrile present in a mixture of the two.

SUMMARY OF THE INVENTION

This invention is such a simple and economical process comprising the isomerization of a dinitrile selected from the group consisting of fumaronitrile and maleonitrile in the presence of a nitrile solvent and a base to produce the corresponding geometric isomer of the isomerized dinitrile.

It is surprising that an isomerization reaction will take place in the absence of expensive catalysts and under mild reaction conditions. It is also surprising that fumaronitrile and maleonitrile isomerize under these conditions rather than reacting with the nitrile solvent.

DETAILED DESCRIPTION OF THE ILLUSTRATIVE EMBODIMENTS

The process of this invention whereby fumaronitrile is isomerized to produce maleonitrile may be simply represented by the following equation.

Reaction 1

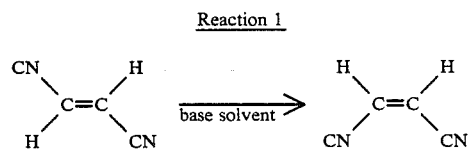

The fumaronitrile which is isomerized by the practice of this invention may be obtained commercially. The fumaronitrile or maleonitrile to be used in the process of this invention may additionally be supplied as a mixture of fumaronitrile and maleonitrile. This mixture may be the product of processes for the preparation of mixtures of the dinitriles. Examples of such processes include the ammoxidation of butene as taught in U.S. Pat. No. 4,436,671 and the oxidative dehydrogenation of succinonitrile as taught in U.S. Pat. No. 3,313,840. The relative proportions of fumaronitrile and maleonitrile may vary depending on the desired result. In any case, the percentage of either isomer in the mixture cannot be increased above about 50 percent by the practice of this invention. This is thought to be due to the thermodynamics of the equilibrium between the two isomers. In those instances where it is desired to produce maleonitrile by the isomerization of fumaronitrile, it is preferred to use pure fumaronitrile which may be obtained commercially.

A solvent is used in the practice of this invention and is preferably one corresponding to the formula $$R(CN)_n$$

where R is a hydrocarbyl radical with a valency equal to n and n is an integer equal to 1 or 2. It is preferred that R is alkyl and that n is 1. It is more preferred that R is lower alkyl. Examples of solvents useful in the practice of this invention include propionitrile, butyronitrile, succinonitrile and acetonitrile. It is most preferred to use acetonitrile as the solvent.

Bases useful in the practice of this invention are any which will allow the isomerization reaction to proceed. Examples of bases useful in the practice of this invention include both inorganic and organic bases. Organic bases include, by way of example, amines such as triethylamine, N-methylmorpholine and 1-methylpyrazole and ion exchange resins. Inorganic bases include, by way of example, alkali metal hydroxides such as sodium hydroxide, potassium hydroxide, cesium hydroxide and lithium hydroxide; and alkaline earth metal oxides such as magnesium oxide and calcium oxide. As a base, it is preferred to use alkali earth metal hydroxides and it is most preferred to use potassium hydroxide. The base may be used in any form which will allow the isomerization reaction to proceed. It is preferred to use the base in solid form.

Any relative amounts of the dinitrile to be isomerized, the solvent and the base may be used which will allow the isomerization reaction to proceed. In the context of this invention, dinitrile means fumaronitrile, maleonitrile or mixtures thereof. The amount of solvent used is not critical so long as a sufficient amount is used to dissolve the reactant. It is preferred that the solvent be present in at least a weight ratio of at least 10:1 of solvent to dinitrile and no greater than a weight ratio of about 50:1 based on the dinitrile. It is more preferred that the weight ratio range from about 15:1 to about 35:1. The molar ratio of the dinitrile to base is preferred to range from about 1:100 to 100:1. It is more preferred that the molar ratio of the dinitrile to base range from about 10:1 to about 1:1.

Any temperature and pressure at which the isomerization reaction will occur is useful in the practice of this invention. The temperature is preferably less than the boiling point of the solvent. In a preferred embodiment where the solvent used is acetonitrile, the temperature is preferably less than about 80° C. The process is more preferably operated at room temperature and pressure for the sake of convenience.

The process may be conducted for any length of time sufficient to convert at least about 10 mole percent of the dinitrile to its corresponding geometric isomer. It is preferred that the reaction run at least about 0.5 hours and no more than about 4 hours. It is more preferred that the reaction run about one hour.

The amount of the dinitrile which reacts by the process of this invention is preferably at least about 10 mole percent. It is more preferably at least about 40 mole percent. In the embodiment of this invention where fumaronitrile is isomerized to maleonitrile, it is preferred that at least about 80 mole percent of the amount of fumaronitrile reacting is converted to maleonitrile. It is more preferred that the selectivity to maleonitrile is about 95 mole percent.

The product produced by the process of this invention is the geometric isomer of the dinitrile reactant. Unreacted dinitrile, solvent and base are also present at the end of the reaction and may be recycled without additional purification following separation by means known to those in the art. In addition to the desired product, a polymer is also produced under some conditions. It is preferred that the amount of polymer formed is no more than about 15 mole percent based on the total moles of fumaronitrile, maleonitrile and polymer present. More preferably, the amount of polymer formed is no more than about 10 mole percent and most preferably the amount of polymer formed is less than about 1 mole percent.

At the end of the reaction, the base is removed from the reaction mixture by means known to those in the art. The method by which the base is removed is not crucial to the practice of this invention. Examples of methods by which the base is removed include decantation or filtration. The maleonitrile is separated from the fumaronitrile and solvent by conventional means. Vacuum distillation is one example of how the dinitriles may be separated. The dinitrile reactant which has not been converted to its geometric isomer and the solvent may be recycled for additional isomerization without being separated or undergoing any additional treatment or purification.

It is preferred that the reaction is carried out with continuous stirring and under an inert atmosphere, more preferably a nitrogen purge.

The process may be conducted in a batch mode or it may be run continuously. In a continuous method, the dinitrile and solvent are mixed and allowed to flow over the base. In this way, the flow rate of the dinitrile and solvent is used to control the amount of contact time and thus the extent of the reaction. It is preferred to run the reaction in a continuous mode using a plug flow reactor or a continuous stirred tank. Residence times are preferred to be no more than about 0.5 hours.

In a preferred embodiment, maleonitrile is produced from the isomerization of fumaronitrile. Fumaronitrile and acetonitrile are mixed and allowed to flow over potassium hydroxide pellets and the flow rate is used to control the reaction time. The maleonitrile is removed from the fumaronitrile and acetonitrile by vacuum distillation. Then the fumaronitrile and acetonitrile are recycled for further isomerization.

The following illustrative examples are provided to more fully explain the invention, but not to limit the invention in any way. Unless stated otherwise, all parts and percentages are by weight.

EXAMPLE 1

Isomerization of Fumaronitrile to Maleonitrile

Fumaronitrile (2.2 g), obtained commercially, is recrystallized from toluene and dissolved in 100 ml of acetonitrile. It is then added to a flask equipped with a magnetic stirrer and containing 1.0 g of NaOH as solid pellets. The reaction is continuously stirred, conducted under a nitrogen purge and the temperature is 20° C. Immediately upon the addition of the fumaronitrile and acetonitrile, the reaction mixture turns dark. After 4 hours, a sample of the reaction mixture is analyzed on a Hewlett-Packard 5790 gas chromatograph with a flame ionization detector. The mixture contains 86.6 mole percent of fumaronitrile and 13.4 mole percent of maleonitrile.

EXAMPLE 2

Example 1 is repeated with the substitution of 1.5 g KOH for the NaOH and the reaction mixture is sampled and analyzed after 1 hour and after 3 hours. The mixture contains 80.0 mole percent fumaronitrile and 13.4 mole percent maleonitrile after one hour of reaction and 53.8 mole percent fumaronitrile and 46.2 mole percent maleonitrile after three hours. The product analyzed at three hours also contains a small amount of polymer.

EXAMPLE 3

Example 2 is repeated using 1.6 g of CsOH in place of the KOH and 5.0 g of fumaronitrile in 150 ml of acetonitrile. The reaction mixture is sampled at 20 minutes and analyzed to show 72.0 mole percent of fumaronitrile and 28.0 mole percent of maleonitrile. An unmeasured amount of polymer is also present.

EXAMPLE 4

Example 3 is repeated using 1.5 g of CsOH and 7.8 g of fumaronitrile. The reaction mixture is maintained at 80° C. instead of 20° C. The reaction mixture is analyzed after four hours and shows 64.5 mole percent fumaronitrile and 35.5 mole percent maleonitrile.

EXAMPLE 5

Example 1 is repeated with the exception that the reaction mixture is not stirred. The reaction mixture is sampled at 5 hours and at 6 hours. After 5 hours, the analyzed product shows 86.5 mole percent fumaronitrile, 5.3 mole percent maleonitrile and 8.1 mole percent polymer. After 6 hours, the analyzed product shows 89.3 mole percent fumaronitrile, 6.3 mole percent maleonitrile and 4.4 mole percent polymer.

EXAMPLE 6

Example 5 is repeated using 1.0 g of KOH in place of the NaOH and the reaction mixture is sampled at 1.5, 4 and 5 hours. After 1.5 hours, the analyzed product shows 96.7 mole percent fumaronitrile, 0.5 mole percent maleonitrile and 2.8 mole percent polymer. After 4 hours, the analyzed product shows 92.1 mole percent fumaronitrile, 5.0 mole percent maleonitrile and 2.9 mole percent polymer. After 5 hours, the analyzed product shows 88.0 mole percent fumaronitrile, 8.0 mole percent maleonitrile and 4.0 mole percent polymer.

EXAMPLE 7

Example 6 is repeated using 1.1 g of CsOH in place of the KOH and reaction mixture is sampled at 1.8 hours and 5.7 hours. After 1.8 hours, the analyzed product shows 87.8 mole percent fumaronitrile, 6.4 mole percent maleonitrile and 3.8 mole percent polymer. After 5.7 hours, the analyzed product shows 62.7 mole percent fumaronitrile, 22.7 mole percent maleonitrile and 14.6 mole percent polymer.

A comparison of the data shown in Examples 1-4 with that from Examples 5-7 demonstrates that the rates of formation of maleonitrile and polymer are each increased when the reaction mixture is stirred. The data also shows that the use of KOH or CsOH rather than NaOH results in the formation of a larger amount of maleonitrile. The data also shows that the use of CsOH as base results in the formation of more polymer than the use of KOH under similar conditions.

What is claimed is:

1. A process for the isomerization of fumaronitrile consisting essentially of mixing fumaronitrile, an inert nitrile solvent corresponding to the formula $$R(CN)_n$$

wherein R is a hydrocarbyl radical with a valency equal to n and n is 1 or 2, and a base under reaction conditions such that a product mixture containing fumaronitrile and no more than about fifty mole percent maleonitrile is produced.

2. The process of claim 1 wherein the solvent is selected from the group consisting of propionitrile, butyronitrile, succinonitrile and acetonitrile.

3. The process of claim 2 wherein the solvent is acetonitrile.

4. The process of claim 1 wherein the base is an alkali metal hydroxide.

5. The process of claim 4 wherein the base is potassium hydroxide.

6. The process of claim 1 wherein the base is in solid form.

7. The process of claim 1 wherein the isomerization takes place at room temperature and atmospheric pressure.

8. The process of claim 1 wherein the fumaronitrile and the solvent are separated from the maleonitrile and recycled for further reaction without additional treatment or purification.

9. The process of claim 1 wherein at least about 10 mole percent of the fumaronitrile is converted by the process of this invention.

10. The process of claim 9 wherein at least about 40 mole percent of the fumaronitrile is converted by the process of this invention.

11. The process of claim 10 wherein at least about 80 mole percent of the fumaronitrile converted is converted to maleonitrile.

12. The process of claim 11 wherein at least about 95 mole percent of the fumaronitrile converted is converted to maleonitrile.

13. The process of claim 1 wherein the isomerization reaction is carried out under an inert atmosphere.

14. The process of claim 1 wherein the isomerization reaction is carried out with continuous stirring.

15. The process of claim 1 wherein the reaction is allowed to proceed for at least about 0.5 hour and for no more than about 4 hours.

16. The process of claim 15 wherein the reaction is allowed to proceed for about 1 hour.

17. The process of claim 1 wherein the reaction is carried out on a continuous basis.

18. The process of claim 1 wherein fumaronitrile and acetonitrile are mixed and allowed to flow over potassium hydroxide pellets in a plug flow reactor with a residence time of about 0.5 hours forming maleonitrile which is separated from the fumaronitrile and acetonitrile by vacuum distillation.

19. A process for the isomerization of maleonitrile consisting essentially of mixing the maleonitrile, an inert nitrile solvent corresponding to the formula $$R(CN)_n$$

wherein R is a hydrocarbyl radical with a valency equal to n and n is 1 or 2, and a base under reaction conditions such that a product mixture containing maleonitrile and no more than about fifty mole percent fumaronitrile is produced.

20. A process wherein a two-component mixture consisting essentially of fumaronitrile and maleonitrile in which the fumaronitrile and maleonitrile components are present in unequal mole percentages is subjected to an isomerization reaction to increase the percentage in the mixture of the mixture component which is present in the mixture in the smaller amount, said reaction consisting essentially of mixing the fumaronitrile and maleonitrile mixture, an inert nitrile solvent corresponding to the formula $$R(CN)_n$$

wherein R is a hydrocarbyl radical with a valency equal to n and n is 1 or 2, and a base under reaction conditions such that a product mixture containing an increased percentage of the mixture component originally present in the smaller percentage is produced, provided that the percentage of the mixture component originally present in the smaller amount is increased to no more than about fifty mole percent.

* * * * *